US010948500B2

(12) United States Patent
Warthoe

(10) Patent No.: US 10,948,500 B2
(45) Date of Patent: Mar. 16, 2021

(54) METHOD FOR DETERMINING THE QUANTITY OF AN HBA1C IN A BLOOD SAMPLE

(71) Applicant: W. Health L.P., Nassau (BS)

(72) Inventor: Peter Warthoe, Copenhagen Ø (DK)

(73) Assignee: W. Health L.P., Nassau (BS)

( * ) Notice: Subject to any disclaimer, the term of this patent is extended or adjusted under 35 U.S.C. 154(b) by 136 days.

(21) Appl. No.: 16/066,383

(22) PCT Filed: Dec. 29, 2016

(86) PCT No.: PCT/EP2016/082830
§ 371 (c)(1),
(2) Date: Jun. 27, 2018

(87) PCT Pub. No.: WO2017/114893
PCT Pub. Date: Jul. 6, 2017

(65) Prior Publication Data
US 2019/0018024 A1  Jan. 17, 2019

(30) Foreign Application Priority Data
Dec. 30, 2015 (DK) .......................... PA 2015 00848

(51) Int. Cl.
*G01N 33/72* (2006.01)
*G01N 33/542* (2006.01)
*G01N 21/64* (2006.01)

(52) U.S. Cl.
CPC ....... *G01N 33/723* (2013.01); *G01N 21/6428* (2013.01); *G01N 21/6486* (2013.01); *G01N 33/542* (2013.01)

(58) Field of Classification Search
CPC ...... G01N 33/49; G01N 33/542; G01N 33/72; G01N 33/721; G01N 33/723; G01N 21/64;
(Continued)

(56) References Cited

U.S. PATENT DOCUMENTS 5,478,754 A * 12/1995 Brandt ................ G01N 33/723
436/518
5,541,117 A  7/1996 Karl et al.
(Continued)

FOREIGN PATENT DOCUMENTS

EP   0455225 A2   11/1991
EP   0772779 B1    5/2000
(Continued)

OTHER PUBLICATIONS

Blincko et al. Ann. Clin. Biochem., vol. 37, 2000, pp. 492-497.*
(Continued)

*Primary Examiner* — Maureen Wallenhorst
(74) *Attorney, Agent, or Firm* — Ziegler IP Law Group, LLC

(57) ABSTRACT

Methods and kits-of-parts for determining the quantity of HbA1c relative to the concentration of haemoglobin in a blood sample which includes less than 200 μl of blood, the method including the steps of adding the fluorophore to the sample and measuring the fluorescence at one or more time points within the time interval, at which the change in fluorescence over time is >0, followed by measurements of haemoglobin by adding a haemoglobin-binding agent and measuring the change in transmission at approximately 570 nm and comparing the obtained results with an internal standard.

12 Claims, 7 Drawing Sheets

(58) Field of Classification Search
CPC . G01N 21/6428; G01N 21/6486; G01N 21/59
USPC ............. 436/63, 66, 67, 164, 172; 422/430
See application file for complete search history.

(56) References Cited

U.S. PATENT DOCUMENTS

| | | | |
|---|---|---|---|
| 5,877,025 A | | 3/1999 | Edwards et al. |
| 5,919,708 A | * | 7/1999 | Sundrehagen ......... G01N 33/68 436/66 |
| 6,818,416 B2 | * | 11/2004 | Pachl .................... G01N 33/558 435/25 |
| 2005/0142332 A1 | | 6/2005 | Sauer |
| 2009/0176309 A1 | | 7/2009 | Vessey et al. |
| 2011/0269147 A1 | * | 11/2011 | Chinnayelka ......... G01N 33/542 435/7.1 |

FOREIGN PATENT DOCUMENTS

| | | |
|---|---|---|
| EP | 2433140 B1 | 2/2015 |
| WO | 2010009459 A1 | 1/2010 |
| WO | 2014147395 A1 | 9/2014 |

OTHER PUBLICATIONS

Bincko et al. "Non-separation assay for glycohemoglobin" Clinical Chemistry, Jun. 1, 1998, vol. 44, No. 6, pp. 1302-1308, Retrieved from Internet: URL: http://clincham.aaccjnls.org/content/clinchem/44/6/1302.full.pdf, 7 pages.

Oshiro et al "New Method for Hemoglobin Determination by Using Sodium Lauryl Sulfate (SLS)", Clinical Biochemistry, 1982, vol. 15, No. 1, 6 pages.

Roche Diagnostsics GMBH "cobas HbA1c Test", Apr. 1, 2014, Retrieved from Internet: URL: https://pim-eservices.roche.com/eLD/(S(oftjrleuu4mza4lanlcmabwx))/mt/tr/Documents/GetDocument?documentId=83cde70a-def5-e311-98a1-00215a9b0bba8, 3 pages.

International Search Report, Application No. PCT/EP2016/082830, dated Feb. 22, 2017, 3 pages.

Written Opinion of the International Searching Authority, Application No. PCT/EP2016/082830, dated Feb. 22, 2017, 7 pages.

Danish Patent and Trademark Office, Search Report, Application No. PA 2015 00848, dated Aug. 17, 2016, 4 pages.

* cited by examiner

METHOD FOR DETERMINING THE QUANTITY OF AN HBA1C IN A BLOOD SAMPLE

FIELD

The aspects of disclosed embodiments relate to a method for determining the quantity of HbA1c in a blood sample comprising less than 200 µl. Further, the invention relates to a kit-of-parts for determining the quantity of HbA1c in a sample.

BACKGROUND

Glycated haemoglobin (HbA1c or haemoglobin A1c, HbA1c, A1C, or Hb1c) is a natural form of haemoglobin that is measured primarily to identify the average plasma glucose concentration over prolonged periods of time in humans. HbA1c is formed in a non-enzymatic glycation pathway by haemoglobin's exposure to plasma glucose. As the average amount of plasma glucose increases, the fraction of glycated haemoglobin increases in a predictable way. Thus, the blood level of HbA1c serves as a marker for the average glucose concentration in the blood of a patient in the months prior to the measurement, and is relatively insensitive towards natural daily fluctuations in the glucose level, e.g. due to exercise, rest, meals and other behavioural influences on the glucose level. Thus, HbA1c has been suggested as a marker of the general health state of the individual patient.

Correctly assessing the quantity of HbA1c in blood samples from patients poses ubiquitous challenges to medicinal practitioners. A high amount of glycated haemoglobin indicates poor control of blood glucose levels, which has been associated with cardiovascular disease, nephropathy, and retinopathy. Especially in type 1 and 2 diabetic patients, the monitoring of HbA1c may improve diagnosis and treatment.

Conventional methods for measuring HbA1c in blood samples include column-based borate affinity, HPLC affinity, immunoassay and borate fluorescence quenching methods where a change in fluorescence in liquids containing fluorophores is induced by the selective binding of HbA1c to the fluorophore. The change in measurements of fluorescence after exposure to the HbA1c-containing sample is evaluated and correlated with the relative presence of haemoglobin.

US 2009/0176309 and U.S. Pat. No. 5,877,025 disclose such methods and describe the use of photoluminescent or chemiluminescent marker compound containing a boronic acid group that reacts selectively with a glycated protein (such as HbA1c).

A method for determining the concentration of total haemoglobin is to use conventional photometric measurements of the absorbance at 405 or 415 nm as disclosed e.g. in EP 0 772 779. Another method is to measure total haemoglobin at the isosbestic point (nm).

However, conventional methods provide unsatisfactory results in terms of accuracy and reproducibility, especially when used in connection with small volume samples. Reproducibility is particularly important for using the HbA1c analyte as a monitoring tool for diabetes patients. It is preferable to have % CV-values below 4%, such as less than 3.5% (NGSP standard).

Thus, there is a constant need in the art for alternative methods for determining HbA1c, especially methods that provide increased accuracy and give increased reproducibility. The aspects of the disclosed embodiments are directed to providing such methods.

Measurements of analytes in blood samples by patient- and user-friendly equipment conventionally aim at analysing blood samples consisting of less than 200 µl blood. Such quantities are easily obtained by the individual patients without being associated with serious health risks.

Thus, there is a need in the art for methods and devices capable of analysing HbA1c quantities in blood samples comprising less than 200 µl blood. Even more specifically, there is a need in the art for methods and devices capable of analysing HbA1c quantities in blood samples comprising less than 180 µl blood, such as less than 150 µl, such as less than 100 µl, such as less than 50 µl, such as less than 20 µl, such as less than 10 µl, such as less than 9 µl, such as less than 8 µl, such as less than 7 µl, such as less than 6 µl, such as less than 5 µl, such as less than 4 µl, such as less than 3 µl, such as 2 µl or less blood. It is an object of the invention to provide such methods.

Another challenge is to increase the ease of each analysis, preferably to a level at which measurements of HbA1c in blood can be made by the patient without the assistance of medicinal practitioners. Further, it is also a challenge to bring down the costs to a level at which each measurement is affordable by the consumer.

Accordingly, there is a need in the art for methods and patient-friendly kits-of-parts allowing individual patients to accurately and easily measure the level of HbA1c in blood samples. Further, there is a need in the art for methods and kits-of-parts that allow for a simple and easy handling of samples and blood analysis. The aspects of the disclosed embodiments are directed to providing such methods and kits-of-parts.

SUMMARY

As stated above, there is a ubiquitous need in the art for methods and patient-friendly kits-of-parts providing accurate, sensitive and reproducible measurements of the level of HbA1c in blood samples. It is an object of the invention to provide such kits-of-parts and methods.

Measurements of HbA1c levels in blood samples require two measurements, i.e. a measurement of the amount of HbA1c and a measurement of the total amount of haemoglobin in the sample.

Surprisingly, it was found that improved methods with higher accuracy and higher precision using small amounts of sample could be obtained by measuring the amount of HbA1c in the sample by a fluorophore-binding method, wherein the fluorescence measurements were made at a specific time ($T_{3,4}$) after contact between the sample and the fluorophore, where the fluorescence is decreasing over time, reflecting that not all HbA1c in the sample has been associated with a fluorophore. Said time ($T_{3,4}$) may also be referred to as the binding phase.

Further, it was surprisingly found that improved methods with higher accuracy and higher precision could be obtained by measuring the total haemoglobin concentration by measuring the absorbance at approximately 570 nm after contacting the sample with an agent binding haemoglobin, said measurement being performed in the sample after the amount of HbA1c had been measured.

Thus, the above problems have been solved according to the present invention, which provides a method for determining the quantity of HbA1c relative to the concentration of haemoglobin in a blood sample comprising less than 200 μl the method comprising the steps of:

a. providing a fluorophore comprising a ligand capable of binding HbA1c,
b. providing a buffered liquid,
c. measuring the transmission ($TR_0$) of the buffered liquid at time $T_0$ at a wavelength of approximately 570 nm and optionally measuring the fluorescence ($FLT_0$) of the buffered liquid at a wavelength (X) at which the fluorophore emits fluorescent light when excited,
d. adding the fluorophore to the buffered liquid, thereby creating a buffered reaction liquid, and optionally measuring the fluorescence ($FLT_1$) of the buffered reaction liquid at time $T_1$ at the wavelength X,
e. adding the sample to the buffered reaction liquid at time $T_2$, whereby a first detection liquid is formed comprising a fluorescence complex comprising the fluorophore and HbA1c, and measuring the fluorescence ($FLT_{3,4}$) at the wavelength X of the first detection liquid at one or more time points within the time interval $T_3$-$T_4$, at which the change in fluorescence over time is >0, reflecting that less than all HbA1c in the sample is part of a fluorescence complex in the detection liquid,
f. adding a haemoglobin-binding agent to the first detection liquid at time $T_5$, thereby creating a second detection liquid comprising a complex comprising the haemoglobin binding agent and haemoglobin, and measuring the transmission ($TRT_6$) of the second detection liquid at approximately 570 nm at time $T_6$,
g. determining the absorbance of the sample by dividing the transmission signal ($TRT_6$) with the transmission signal ($TRT_0$),
h. determining the relative quantity of HbA1c by dividing the fluorescence signal ($FLT_{3,4}$), with the absorbance determined in step g), and comparing the obtained results with results obtained using an internal standard sample.

The relative HbA1c concentration vs. the total haemoglobin concentration may be determined by comparing the obtained measurements with results obtained using the same method applying internal standard samples having known concentrations of HbA1c and haemoglobin. Such internal standard samples may be obtained from commercial sources.

BRIEF DESCRIPTION OF THE FIGURES

Embodiments of the present disclosure will be described in more detail in the following with regard to the accompanying figures. The figures show one way of implementing the present invention and are not to be construed as being limiting to other possible embodiments falling within the scope of the attached claim set.

As seen in FIG. 2, the fluorescence continued to decrease, slightly approaching an asymptote at approx. between 80-100 seconds.

DEFINITIONS

Fluorophore

Figure 1:
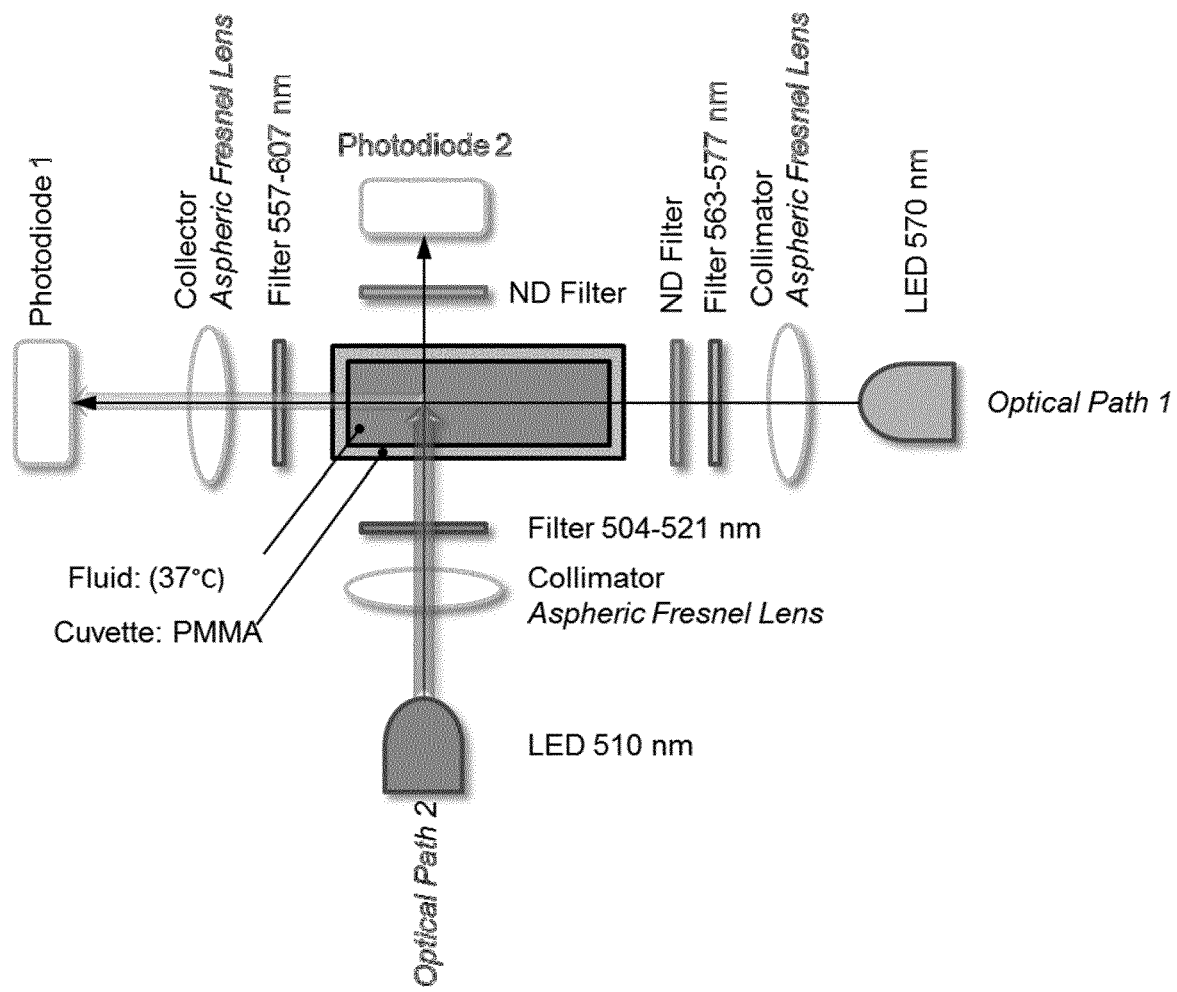
FIG. 1 illustrates the optical system in the measuring device used, hereinafter called "TRACE". The optical system consists of two optical paths. In optical path 1, the transmission is measured at 570 nm using the LED 570 nm at light source and the photodiode 1 as detector. In optical path 2, the light source is the LED 510 and the photodiode 1 is the detector for measuring the fluorescence signal. In addition, the optical path 2 also has a transmission channel measuring the 510 nm signal on photodiode 2.

According to the present disclosure, fluorophore means an agent or means, the presence of which, in a reaction and detection liquid, causes (after being exited) the emission of detectable electromagnetic radiation (light), such as a photoluminescent marker compound. In a preferred embodiment, the fluorophore is an agent that emits detectable light in response to being contacted or irradiated with light.

Blood Sample

According to the present disclosure, blood sample means a sample of full blood from a patient, or a material derived from or comprising red blood cells from a patient.

Ligand

According to the present disclosure, ligand means an agent or means, the presence of which (e.g. on or in association with the fluorophore) causes the binding or association of HbA1c and the fluorophore. In a preferred embodiment, the ligand is an agent that is attached (covalently) to the fluorophore and that is capable of binding to HbA1c. Borate binds selectively to HbA1c and may be attached to several fluorophores. Thus, borate or boronic acid is a suitable ligand according to the present invention. Thus, according to the present invention, a "fluorophore comprising a ligand" means a molecular complex comprising a fluorophore group and a ligand group. U.S. Pat. No. 5,877,025 describes an exemplary fluorophore/ligand complex being a photoluminescent or chemiluminescent marker compound containing a boronic acid group that reacts selectively with glycated proteins such as HbA1c.

Binding Phase

According to the present disclosure, binding phase means the phase wherein the binding or association of HbA1c and the fluorophore occurs, but where binding is not yet completed.

Precision and Accuracy

According to the present disclosure, precision means the ability of a method to generate test results on the concentration of HbA1c (e.g. from multiple runs on the same sample) that do not vary significantly from each other. According to the present invention, accuracy means the ability of a method to generate test results on the concentration of HbA1c, the mean of which does not vary significantly from the true concentration of HbA1c. Methods may have a low accuracy and a high precision meaning that the test consistently give similar results that vary from the true result.

The true results are defined according to the NGSP standards. Methods may also have a high accuracy and a low precision meaning that the test consistently gives dissimilar results, but with a mean result that is similar to the true result. It is highly preferred to obtain and use methods with both a high accuracy and a high precision.

DETAILED DESCRIPTION

Surprisingly, it was found that improved methods with higher accuracy and higher precision could be obtained by measuring the amount of HbA1c in the sample by a fluorophore-binding method, wherein the fluorescence measurements were made at a time ($T_{3,4}$) after contact between the sample and the fluorophore, where the fluorescence is decreasing over time, reflecting that not all HbA1c in the sample has been associated with a fluorophore. Said time ($T_{3,4}$) may also be referred to as the binding phase, where the fluorophore binds to HbA1c through the ligand.

Further, it was surprisingly found that improved methods with higher accuracy and higher precision could be obtained by measuring the total haemoglobin concentration by way of measuring the decrease in absorbance at approximately 570 nm after contacting the sample with an agent capable of binding total haemoglobin, said measurement being performed in the sample after the amount of HbA1c had been measured.

Thus, during the investigations leading to the present disclosure, it was surprisingly observed that it was possible to obtain measurements of HbA1c from blood samples with improved precision and accuracy, and with improved ease by measuring the impact of HbA1c on the fluorescence emitted from a fluorophore under reaction conditions providing a phase of binding of HbA1c to the fluorophore, where after the total haemoglobin content was measured using a method wherein total haemoglobin is bound to a suitable haemoglobin-binding agent providing a detectable decrease in transmission at 570 nm.

Accordingly, the present invention relates to a method for determining the quantity of HbA1c relative to the concentration of haemoglobin in a blood sample comprising less than 200 µl, the method comprising the steps of:

a. providing a fluorophore comprising a ligand capable of binding HbA1c,
b. providing a buffered liquid,
c. measuring the transmission ($TRT_0$) of the buffered liquid at time $T_0$ at a wavelength of approximately 570 nm and optionally measuring the fluorescence ($FLT_0$) of the buffered liquid at a wavelength (X) at which the fluorophore emits fluorescent light when excited,
d. adding the fluorophore to the buffered liquid, thereby creating a buffered reaction liquid, and optionally measuring the fluorescence ($FLT_1$) of the buffered reaction liquid at time $T_1$ at the wavelength X,
e. adding the sample to the buffered reaction liquid at time $T_2$, whereby a first detection liquid is formed comprising a fluorescence complex comprising the fluorophore and HbA1c, and measuring the fluorescence ($FLT_{3,4}$) at the wavelength X of the first detection liquid at one or more time points within the time interval $T_3$-$T_4$, at which the change in fluorescence over time is >0, reflecting that less than all HbA1c in the sample is part of a fluorescence complex in the detection liquid,
f. adding a haemoglobin-binding agent to the first detection liquid at time $T_5$, thereby creating a second detection liquid comprising a complex comprising the haemoglobin binding agent and haemoglobin, and measuring the transmission ($TRT_6$) of the second detection liquid at approximately 570 nm at time $T_6$,
g. determining the absorbance of the sample by dividing the transmission signal ($TRT_6$) with the transmission signal ($TRT_0$),
h. determining the relative quantity of HbA1c by dividing the fluorescence signal ($FLT_{3,4}$), with the absorbance determined in step g), and comparing the obtained results with an internal standard.

The results from the internal standard used in step h) should be results obtained using the exact same method as the method used when generating the sample results. Internal sample results need not to be run each time the method is performed but are preferably obtained previously and provided and stored for the purpose of comparison with subsequent samples. However, it was surprisingly observed that the amount of fluorophore added to the sample had a significant impact on the performance of the method with respect to the comparison with the internal standard in step h).

Adding a well-defined volume of fluorophore to a small volume sample is a difficult task, and in practice, it is impossible to provide kits-of-parts or ready-to-use assays wherein the amount of fluorophore is guaranteed to be precise and uniform between assays.

However, it was surprisingly found that the fluorescence measurements made in the binding phase ($FLT_{3,4}$) in the method according to the present disclosure could be corrected by a pre-determined factor, said factor depending on the actual amount of fluorophore present in the sample. Thus, by incorporating a multiplication factor correcting the actually obtained fluorescence signal for amount of fluorophore used, each individual sample run could be compared to an internal standard irrespective of variations in added fluorophore with much higher accuracy and precision.

Thus, in a preferred aspect, the aspects of the disclosed embodiments relate to a method wherein the amount of fluorophore added to the liquid in step d) is determined by measuring the fluorescence ($FLT_1$) of the liquid in step d), and the fluorescence signal ($FLT_{3,4}$) is corrected for amount of fluorophore added. The correction factor to be applied in each case varies according to individual embodiments of the invention (specific assay conditions such as temperature, buffer, fluorophore used etc.) but may be determined readily for each specific assay. Such correction factors may be predetermined for each specific assay such that they are ready to be applied in later assays with unknown amount of added (actual) amount of fluorophore.

Further, according to the aspects of the disclosed embodiments, it was observed that the precision and accuracy of the method was higher when the fluorescence decrease ($FLT_{3,4}$) was determined shortly after formation of the fluorophore-HbA1c complex.

Thus, in a preferred embodiment of the aspects of the disclosed embodiments, the measurements of the fluorescence decrease ($FLT_{3,4}$) of the detection liquid at time $T_3$-$T_4$ are performed in the binding phase, at a time where more than 1% but less than 85% of HbA1c is bound in a complex comprising the fluorophore.

It is even more preferred that the measurements of the fluorescence decrease ($FLT_{3,4}$) of the detection liquid at times $T_3$-$T_4$ are performed in the binding phase, at a time where more than 1% but less than 75% of HbA1c is bound in a complex comprising the fluorophore.

It is even more preferred that the measurements of the fluorescence decrease ($FLT_{3,4}$) of the detection liquid at times $T_3$-$T_4$ are performed in the binding phase, at a time where more than 1% but less than 60% of HbA1c is bound in a complex comprising the fluorophore.

It is even more preferred that the measurements of the fluorescence decrease ($FLT_{3,4}$) of the detection liquid at times $T_3$-$T_4$ are performed in the binding phase, at a time where more than 1% but less than 50% of HbA1c is bound in a complex comprising the fluorophore.

In a preferred embodiment, at least one measurement of the fluorescence decrease ($FLT_{3,4}$) of the detection liquid at times $T_3$-$T_4$ is performed in the binding phase, at a time where more than 1% but less than 10% of HbA1c is bound in a complex comprising the fluorophore, i.e. at least one measurement is performed immediately after the addition of the fluorophore.

Accordingly, the aspects of the disclosed embodiments relate to a method wherein the time interval $T_3$-$T_4$, is a time interval of 0-30, such as 0-20 seconds after adding the sample to the buffered reaction liquid at time $T_2$. Even more preferably, the time interval $T_3$-$T_4$, is a time interval of 0-15 seconds after adding the sample to the buffered reaction liquid at time $T_2$. Even more preferably, the time interval $T_3$-$T_4$, is a time interval of 0-15 seconds after adding the sample to the buffered reaction liquid at time $T_2$.

The measurements of the fluorescence ($FLT_{3,4}$), comprise measurements at at least two time points within the time interval $T_3$-$T_4$-such that the decrease over a given time period can be determined. More preferably, the measurements of the fluorescence ($FLT_{3,4}$), comprise measurements at at least three time points within the time interval $T_3$-$T_4$, thereby improving the accuracy of the measured decrease. Even more preferably, the measurements of the fluorescence ($FLT_{3,4}$), comprise measurements at at least four time points within the time interval $T_3$-$T_4$, thereby improving the accuracy of the measured decrease.

The relative HbA1c concentration vs. the total haemoglobin concentration may then be determined by measuring the total haemoglobin concentration and calculating the relative concentrations.

Measurements of Transmission at Approximately 570 nm

It was found that improved accuracy and precision could be obtained by measuring the amount of haemoglobin in the sample using a method in which the sample is contacted with an agent binding haemoglobin and measuring the change in transmission of the sample at approximately 570 nm. In contrast to the measurements of fluorescence according to the invention, the time at which the measurements of transmission of the sample (after addition of the haemoglobin-binding agent) was made was found to be of little importance to the performance of the method.

In practice, the measurement of transmission is performed by illuminating the liquid by use of a light source (and preferably also a filter) emitting (and filtering) light at around 570 nm, and detecting the amount of light transmitted at approximately the same wavelength.

The method according to the aspects of the disclosed embodiments require at least two transmission measurements; a first measurement (T1) which serves as a baseline measurement of the sample, and a subsequent measurement (T2) after addition of the agent binding total haemoglobin which, after comparison with the baseline measurement, measures the change in transmission caused by addition of the agent binding haemoglobin to the sample. The change in transmission may subsequently be used to determine the absorbance of the sample, which is a direct measurement of the concentration of haemoglobin in the sample.

Measurements of Fluorescence, Preferably at Approximately 570 nm

It was found that improved accuracy and precision could be obtained by measuring the amount of HbA1c in the sample using a method in which the sample is contacted with HbA1c-binding fluorophore and measuring the change in fluorescence of the sample at approximately the emission wavelength of the fluorophore.

In practice, the measurement of fluorescence is performed by illuminating the liquid by use of a light source (and preferably also a filter) emitting (and filtering) light at around the excitation wavelength of the respective fluorophore, and detecting the fluorescence of the sample at approximately the emission wavelength of the fluorophore.

When using an eosin-containing fluorophore, even though eosin emits light at around 543 nm, it was found possible (without affecting the precision and accuracy of the assay) to measure the fluorescence at the same wavelength as the transmission wavelength, thereby providing a much simpler assay. Thus, in a highly preferred embodiment of the invention, the fluorophore comprises eosin and the fluorescence measurement (X) is performed at 570 nm.

Fluorophore

According to the present disclosure, the term "fluorophore" includes both phosphorescent and fluorescent compounds. It is preferred that the fluorophore has a principal excitation wavelength of from 450 to 800 nm, (i.e. somewhat distant from the principal excitation wavelength of proteins). It is further preferred that the principal fluorescence wavelength is from 450 to 600 nm. It is particularly preferred that the fluorophore contains the residue of a fluorescent compound such as fluorescein or a fluorescein derivative, for example carboxyfluorescein or a chlorofluoreacein. In this case, the excitation wavelength is preferably approximately 480 nm, and the fluorescence is preferably detected at approximately 520 nm. Other complex organic molecules that are chemiluminescent or phosphorescent rather than fluorescent can also be used as luminescent markers in the method of the invention provided that their chemiluminescence or phosphorescence can be selectively quenched by covalent bonding to HbA1c.

Suitable fluorophores include (the figures shown in parentheses are the principal excitation and fluorescence wavelengths) naphthofluorescein (600/672 nm) eosin (522/543 nm), erythrosin (528/553 nm), coumarin and umbelliferone (360/460 nm), derivatives rhodamine derivatives e.g. Rhodamine B (550/585 nm), tetramethyl rhodamine (540/570 nm), texas red derivatives (589/615 nm), lucifer yellow derivatives (420/535 nm) as well as various BODIPY (4.sub.1 4-difluoro-4-bora-3a.sub.1 4a diaza-s-indacine)

derivatives, NBD-halide (4-halogeno-7-nitrobenzo-2-oxa-1.sub.1 3-diazole) derivatives, Lanthanide chelate derivatives, Transition metal chelate derivative, e.g. Ru tris phenanthroline or Ru tris bipyridyl derivatives and phycobiliprotein derivatives.

Excitation light sources and emission measuring diodes (or respective filters) should preferably emit/measure light at around the relevant wavelengths, but need not be precisely aligned with these optimal wavelengths. According to a preferred embodiment of the present invention, the fluorophore comprises eosin (522/543 nm), and the emission fluorescence X is measured at approximately 570 nm, providing a simpler assay.

Ligand Capable of Binding HbA1c

According to the present disclosure, the ligand is any agent capable of selectively joining or binding HbA1c and the fluorophore together.

In a preferred embodiment of the present disclosure, the ligand is borate or boronic acid.

Haemoglobin Binding Agent

According to the present disclosure, the haemoglobin-binding agent is any agent capable of binding all types of haemoglobin.

In a preferred embodiment of the present disclosure, the haemoglobin-binding agent is sodium lauryl sulphate (SDS).

Kit-of-Parts

In another embodiment, the aspects of the disclosed embodiments provide a kit-of-parts for determining the quantity of an HbA1c in a sample, the kit-of-parts comprising; a fluorophore comprising a ligand capable of binding HbA1c, an instruction for implementing the method according to the invention and one or more predetermined values obtained using the method on internal standards with known amounts of HbA1c and haemoglobin for use in step h) of the method.

In a preferred embodiment, the ligand is borate or boronic acid in the kit-of-parts according to the present disclosure.

In a preferred embodiment, the fluorophore comprises eosin in the kit-of-parts according to the present disclosure.

In a preferred embodiment, the kit-of-parts further comprises a set of predetermined correction factors, used for correction for the actual amount of fluorophore added to the sample in step d) of the method.

EXAMPLES

Example 1. The HbA1c Assay and Calibration Procedure

Samples

Six calibrator samples, all representing different levels of HbA1c concentration in human blood, were purchased from Lyphochek Haemoglobin A1c linearity set (BIO-RAD). The six samples from this BIO-RAD kit were dissolved according to the manufacturer's instructions.

The six linearity samples where measured on TRACE and the raw signal values are reported in Table 1 below.

TABLE 1

| Lyphochek Haemoglobin A1c linearity set (BIORAD) | HbA1c fluorescence signal (510/570 nm channel) | Total Haemoglobin absorbance signal (570/570 nm channel) | Final HbA1c result (HbA1c fluorescence signal/total haemoglobin absorbance signal) |
|---|---|---|---|
| Level 1 | 12.490 | 0.3676 | 33.977 |
| Level 2 | 26.110 | 0.3879 | 67.311 |
| Level 3 | 34.221 | 0.3767 | 90.844 |
| Level 4 | 63.199 | 0.3016 | 209.545 |
| Level 5 | 92.770 | 0.3198 | 290.087 |
| Level 6 | 127.944 | 0.3117 | 410.471 |

Table 1 displays the TRACE measurement of six calibrators (BIO-RAD). In column 2, the TRACE fluorescence signals are displayed. In column 3, the total haemoglobin signals are displayed and in column 4, the final TRACE HbA1c raw-signal is displayed. Column 1 shows the six different levels of HbA1c, each level representing a particular HbA1c concentration. Column 2 shows the raw signal of HbA1c reported in the 510 nm fluorescence channel after 20 seconds of measurement of the fluorescence decrease after adding the blood sample. Column 3 shows the haemoglobin absorbance signal reported in the 570 nm absorbance channel after measuring the fluorescence signal and after mixing the SLS solution into the TRACE cuvette. The 570 nm signal was measured in 20 seconds. Column 4 shows the final HbA1c result where the fluorescence signal from column 2 was divided with the absorbance signal from column 3. The signal in column 4 represents the final HbA1c raw signal reported by TRACE.

Assay Procedure

Between t=0 to t=10 seconds, signals from the HbA1c buffer (ammoniumchloride, sodium deoxycholate, sodium azide PH 8.6) were recorded in the TRACE cuvette both in the 510 nm fluorescence channel (optical path 1) measured at photodiode 1 and the 570 nm absorbance channel (optical path 2) using photodiode 2 as illustrated in FIG. 1.

At time t=11, the Eosin-Borate (a fluorescent marker compound containing an HbA1c ligand) was introduced into reaction cuvettes. The reaction liquids in the cuvettes were excited by a 510 nm LED (passing wavelength 504-521 nm) and the fluorescence signal were recorded between t=11 and t=20 seconds for both the optical path 1 (photodiode 1) and optical path 2 (photodiode 2).

At t=21 seconds, the samples (Level 1-6) derived from full blood (2.0 µl in each sample) were added to the cuvettes and mixed with the reaction liquid containing the HbA1c buffer and the Eosin-Boronate components.

Figure 2:
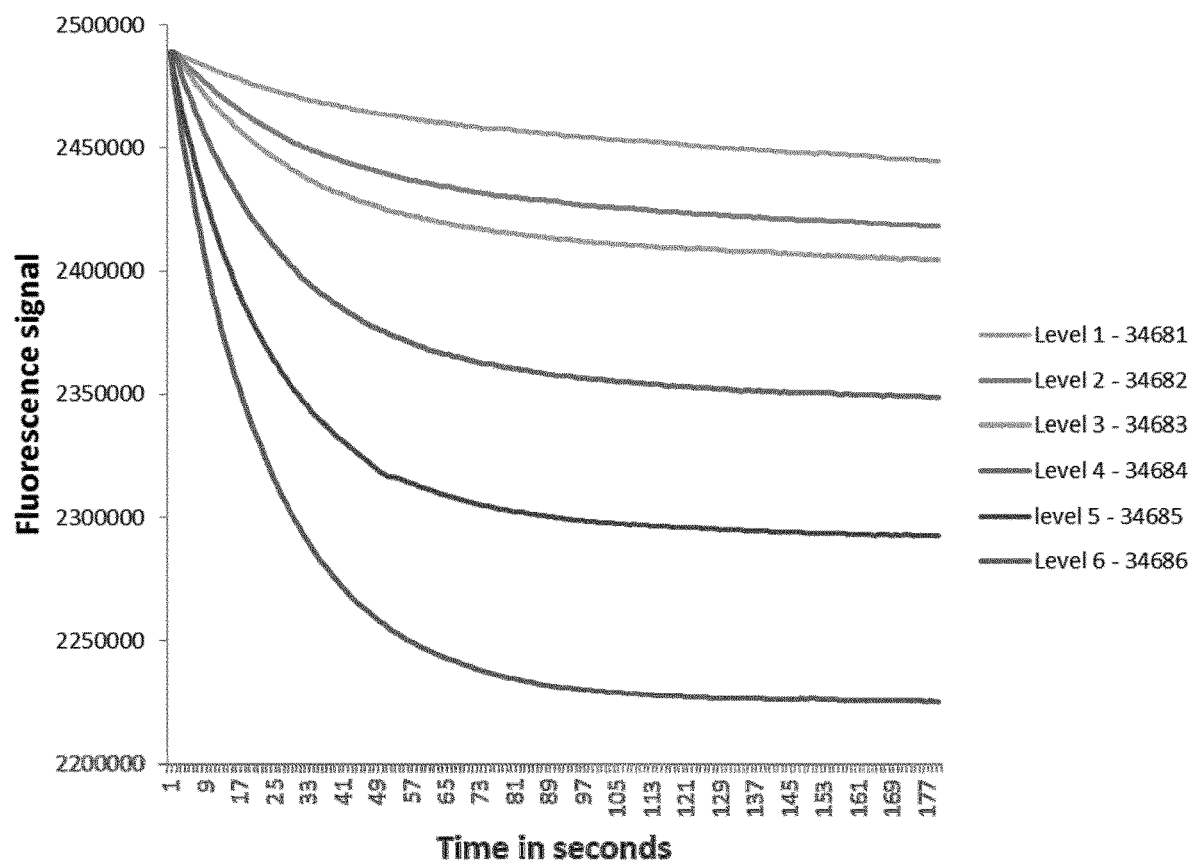
FIG. 2 illustrates six HbA1c standard (BIO-RAD) measurements on TRACE as explained in Example 1. The fluorescence was continuously measured every second from t=21 (when the blood sample was added to the reaction liquid) to t=198 seconds.

The fluorescence was continuously measured every second from t=21 (when the blood sample was added to the reaction liquid) t=198 seconds. As seen in FIG. 2, the fluorescence continued to decrease, slightly approaching an asymptote at approx. between 80-100 seconds.

It was observed that, in this assay, the measurements at time point t=22 seconds to time point t=42 seconds (i.e. 20 seconds after the addition of sample), the fluorescence signal recorded in the fluorescence channel (optical path 1, photodiode 1) showed that approximately 50% of the HbA1c-fluorophore complexes had been formed. Measurements of samples before this time point (20 seconds) were found to provide better correlation to the internal standard than measurements after this time point.

At time point t=45, sodium dodecyl sulphate was introduced into the main cuvette (3 mg/mL HbA1c buffer), and between time t=55 and t=65, the sodium lauryl sulphate-total haemoglobin complex was measured in the absorbance channel (optical path 2, photodiode 2). The final value representing the haemoglobin concentration was calculated at a middle values of the 10 seconds t=55 to t=65 seconds measurement in the 570 nm absorbance channel (optical path 2, photodiode 2). The total haemoglobin concentration was calculated by translating the raw 570 nm signal into absorbance signal using the buffer signal generated between t=0 and t=10 seconds (Abs=2−log(T %)), % T=(570 nm signal t=55 to t=65/570 nm signal t=0 to t=10))*100.

The Final HbA1c signal was recorded as HbA1c=HbA1c (fluorescence signal t=22 to t=42 seconds/absorbance signal t=55 to t=65 seconds).

It should be noted that the fluorescence signal measured between t=11 to t=20, i.e. the amount of fluorophore molecules introduced, may influence the final HbA1c signal, meaning that a correlation factor can be introduced to correlate for this observation when comparing the results obtained in TRACE with the internal standard. Such correlation factors, however, are easily determined and may easily be used when comparing results.

From TRACE Raw-Signal to Final IFCC or NGSP Standard HbA1c Result

Reporting HbA1c values as mmol/mol values are known as the IFCC (International Federation of Clinical Chemistry) units, whereas reporting HbA1c values as % values are known as the NGSP (National Glycohaemoglobin Standardization Program) units.

As illustrated in Table 2, the final TRACE raw-signals are calibrated up against a known standard instrument in the field. In Table 2, the known values according to the IFCC and the NGSP values for the six calibrators measured on the Roche cobas c system (Tina-quant HbA1c assay) are displayed.

TABLE 2

| Lyphochek Haemoglobin A1C linearity set (BIORAD) | Final HbA1c result (HbA1c fluorescence signal/total haemoglobin absorbance signal) | Lyphochek Roche Cobas c system Tina-quant (IFCC - mmol/mol) | Lyphochek Roche Cobas c system Tina-quant (NGSP - %) |
|---|---|---|---|
| Level 1 | 33.977 | 17.1 | 3.71 |
| Level 2 | 67.311 | 29.5 | 4.85 |
| Level 3 | 92.844 | 42.3 | 6.02 |
| Level 4 | 209.087 | 79.1 | 9.39 |
| Level 5 | 209.087 | 116 | 12.7 |
| Level 6 | 410.471 | 161 | 16.8 |

Figure 3:
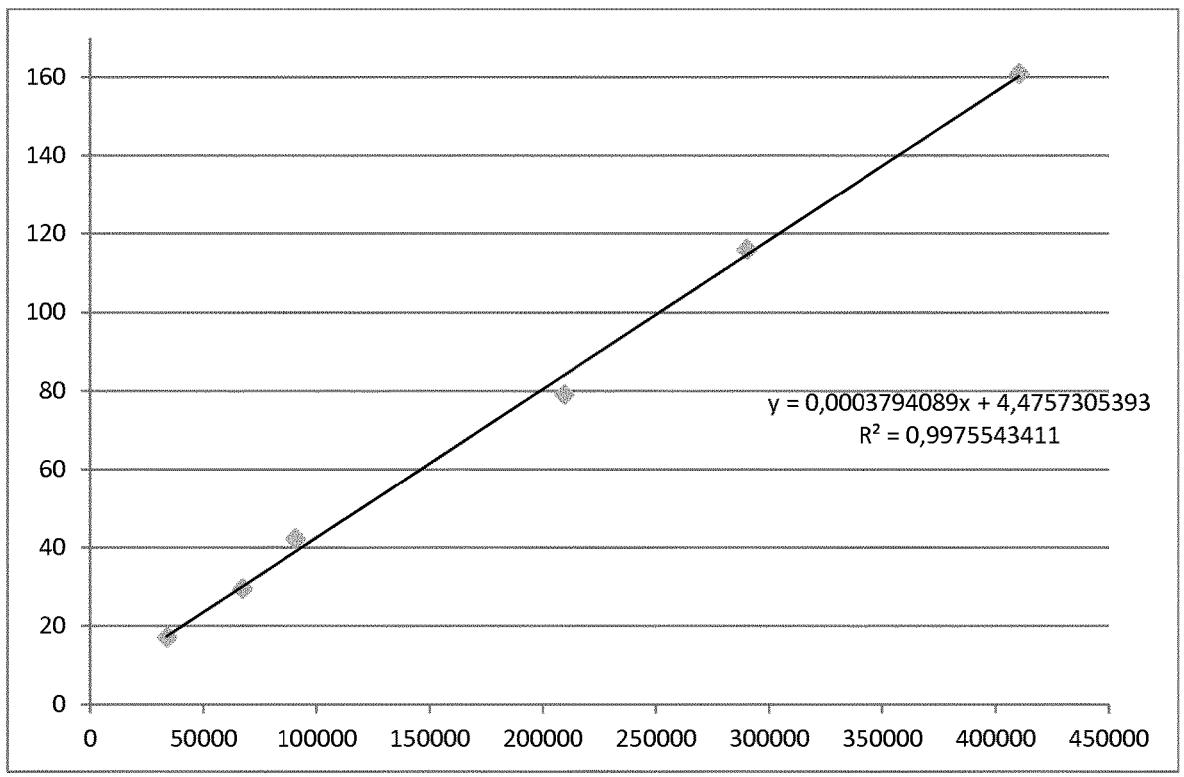
FIG. 3 illustrates the translation from TRACE raw-signal (x-axis) to IFCC units (y-axis) using the Tina-quant HbA1c assay as reference.

TABLE 2 displays the TRACE measurement of six calibrators (BIO-RAD) compared to the reference method (Roche Tina-quant assay) for both the IFCC and the NGSP standards. In FIGS. 3 the 4, the calibration of the final HbA1c values of the assay against the Roche cobas c system (Tina-quant HbA1c assay) is displayed whereas FIG. 3 displays the IFFC calibration and FIG. 4 display the NGSP calibration.

Example 2. The HbA1c Accuracy Procedure 40 patients' samples obtained from Herlev Hospital were measured on TRACE according to Example 1. For each sample, a known value was obtained from the Roche cobas c system (Tina-quant HbA1c assay) reported in NGSP format.

Figure 4:
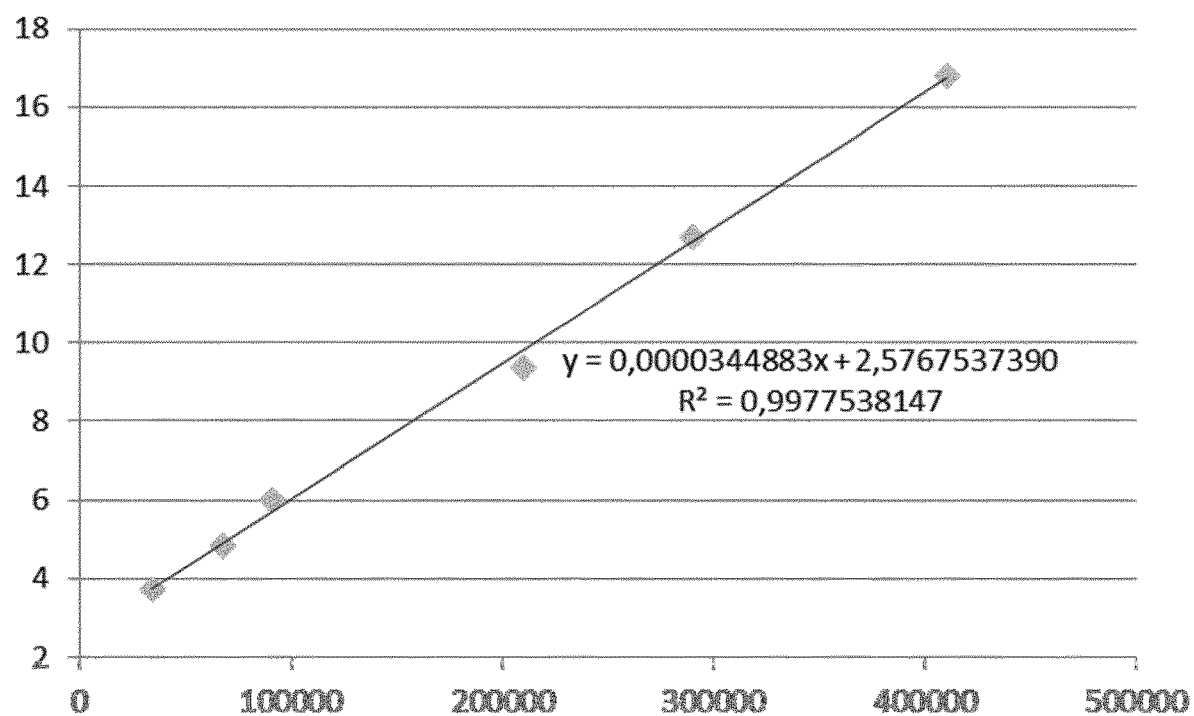
FIG. 4 illustrate the translation from TRACE raw-signal (x-axis) to NGSP units (y-axis) using the Tina-quant HbA1c assay as reference.

In Table 3, the TRACE raw-signals for the 40 patients' samples were translated to 40 NGSP values using the calibration algorithm displayed in FIG. 4.

TABLE 3

40 blood samples from Herlev Hospital

| Blood sample no | TRACE raw signal | TRACE final signal |
|---|---|---|
| 1 | 64937 | 4.8 |
| 2 | 97866 | 6.0 |
| 3 | 63805 | 4.8 |
| 4 | 78532 | 5.3 |
| 5 | 155057 | 7.9 |
| 6 | 114468 | 6.5 |
| 7 | 63982 | 4.8 |
| 8 | 70148 | 5.0 |
| 9 | 118772 | 6.7 |
| 10 | 53626 | 4.4 |
| 11 | 87764 | 5.6 |
| 12 | 76306 | 5.2 |
| 13 | 59218 | 4.6 |
| 14 | 42842 | 4.1 |
| 15 | 43390 | 4.1 |
| 16 | 88154 | 5.6 |
| 17 | 139485 | 7.4 |
| 18 | 47485 | 4.2 |
| 19 | 64388 | 4.8 |
| 20 | 54548 | 4.5 |
| 21 | 70774 | 5.0 |
| 22 | 67455 | 4.9 |
| 23 | 85492 | 5.5 |
| 24 | 217037 | 10.1 |
| 25 | 73790 | 5.1 |
| 26 | 81873 | 5.4 |
| 27 | 79470 | 5.3 |
| 28 | 81301 | 5.4 |
| 29 | 78723 | 5.3 |
| 30 | 123328 | 6.8 |
| 31 | 88694 | 5.6 |
| 32 | 63764 | 4.8 |
| 33 | 155493 | 7.9 |
| 34 | 93030 | 5.8 |
| 35 | 94944 | 5.9 |
| 36 | 103182 | 6.1 |
| 37 | 79319 | 5.3 |
| 38 | 70301 | 5.0 |
| 39 | 99064 | 6.0 |
| 40 | 59951 | 4.6 |

Figure 5:
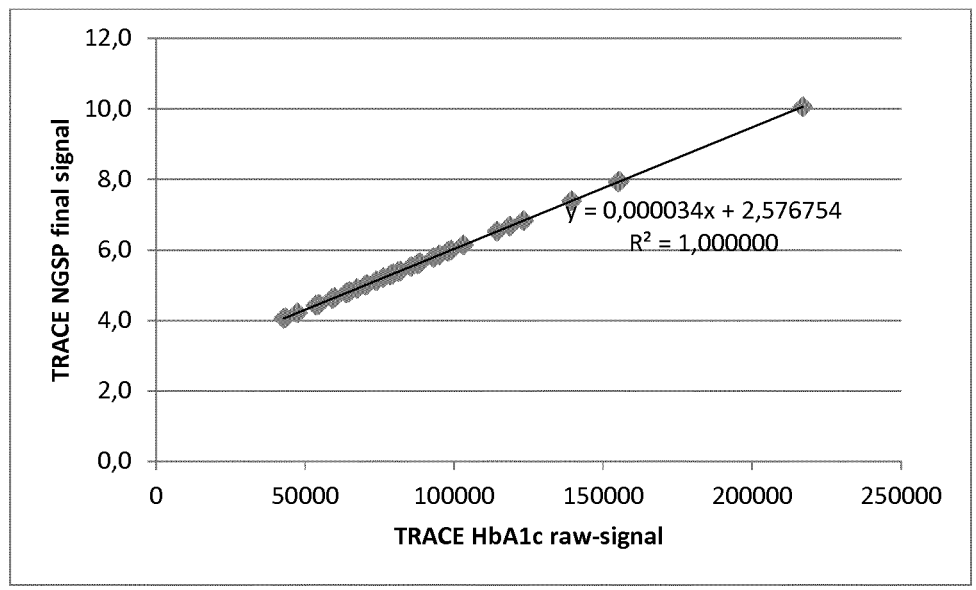
FIG. 5 illustrates 40 patient samples translated from TRACE HbA1c raw-signal (x-axis) to final NGSP unit (y-axis) according to calibration curve illustrated in FIG. 4.

FIG. 5 graphically displays the contents of Table 3, whereas the TRACE HbA1c raw-signal from the 40 patients are displayed (x-axis) as a function of the final TRACE NGSP signal (y-axis).

In Table 4, the 40 patients' run on TRACE are compared with the identical 40 patients' samples run on the Roche cobas c system (Tina-quant HbA1c assay format).

TABLE 4

40 blood samples from Herlev Hospital

| Blood sample no | TRACE | Roche cobas c system |
|---|---|---|
| 1 | 4.8 | 4.9 |
| 2 | 6.0 | 5.9 |
| 3 | 4.8 | 4.9 |
| 4 | 5.3 | 5.5 |
| 5 | 7.9 | 8.0 |
| 6 | 6.5 | 6.4 |
| 7 | 4.8 | 4.9 |
| 8 | 5.0 | 5.2 |
| 9 | 6.7 | 6.5 |
| 10 | 4.4 | 4.2 |
| 11 | 5.6 | 5.8 |

TABLE 4-continued

40 blood samples from Herlev Hospital

| Blood sample no | TRACE | Roche cobas c system |
|---|---|---|
| 12 | 5.2 | 5.5 |
| 13 | 4.6 | 4.8 |
| 14 | 4.1 | 4.2 |
| 15 | 4.1 | 3.9 |
| 16 | 5.6 | 5.7 |
| 17 | 7.4 | 7.2 |
| 18 | 4.2 | 4.2 |
| 19 | 4.8 | 4.8 |
| 20 | 4.5 | 4.5 |
| 21 | 5.0 | 5.1 |
| 22 | 4.9 | 4.9 |
| 23 | 5.5 | 5.4 |
| 24 | 10.1 | 9.9 |
| 25 | 5.1 | 5.1 |
| 26 | 5.4 | 5.4 |
| 27 | 5.3 | 5.5 |
| 28 | 5.4 | 5.4 |
| 29 | 5.3 | 5.3 |
| 30 | 6.8 | 6.8 |
| 31 | 5.6 | 5.6 |
| 32 | 4.8 | 4.9 |
| 33 | 7.9 | 7.9 |
| 34 | 5.8 | 5.8 |
| 35 | 5.9 | 6.0 |
| 36 | 6.1 | 6.1 |
| 37 | 5.3 | 5.3 |
| 38 | 5.0 | 5.0 |
| 39 | 6.0 | 6.1 |
| 40 | 4.6 | 4.4 |

Figure 6:
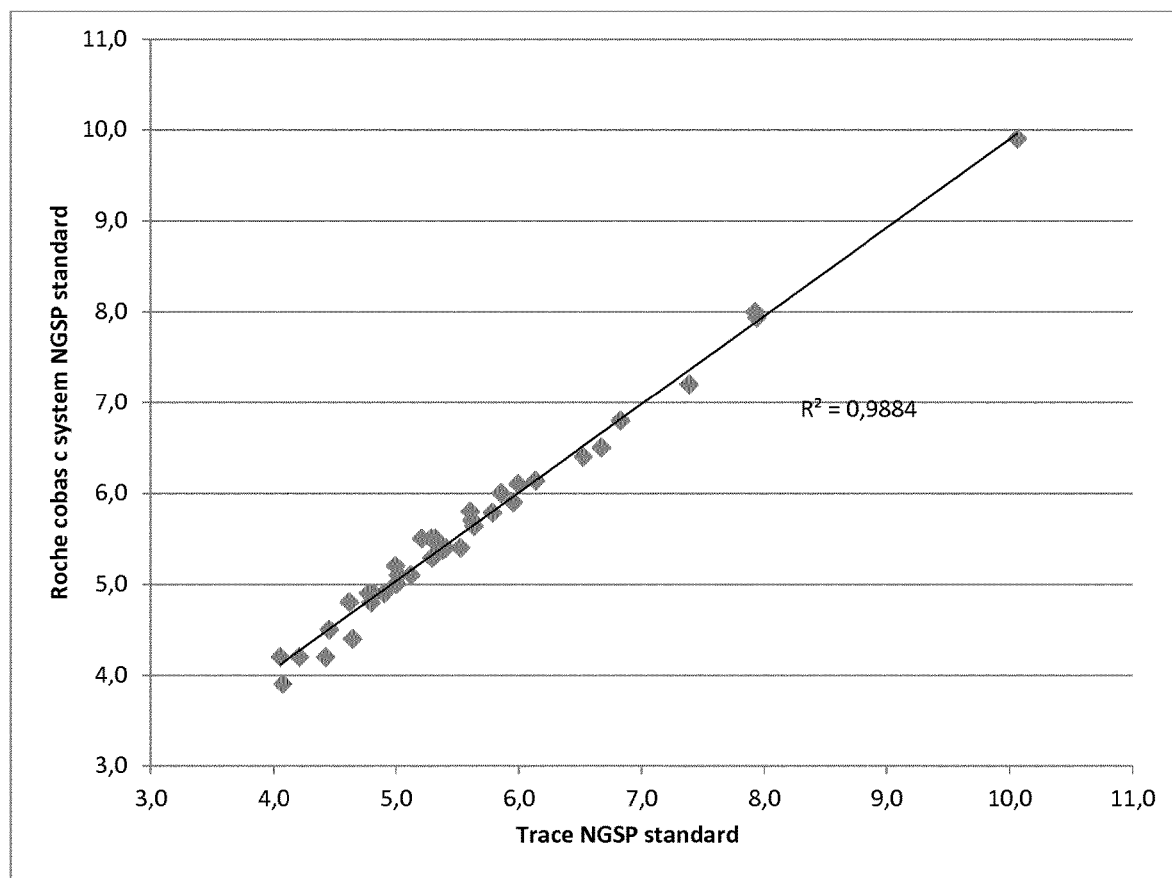
FIG. 6 graphically displays the contents of Table 4, whereas the TRACE HbA1c NGSP results from the 40 patients are displayed (x-axis) as a function of the final TRACE NGSP signal (y-axis) from the Roche cobas c system (Tina-quant HbA1c assay format).

FIG. 6 graphically displays the contents of Table 4, whereas the TRACE HbA1c NGSP results from the 40 patients are displayed (x-axis) as a function of the final TRACE NGSP signal (y-axis) from the Roche cobas c system (Tina-quant HbA1c assay format).

It can be observed from FIG. 6 that a nice correlation exists between the two assay formats—TRACE HbA1c assay format versus Tina-quant HbA1c assay format.

In Table 5, the bias between the TRACE and Tina-quant HbA1c assay format is calculated both in real values (column 4) and in % values (column 5).

TABLE 5

40 blood samples from Herlev Hospital

| Blood sample no | TRACE | Roche cobas c system | Bias | Variation in % |
|---|---|---|---|---|
| 1 | 4.8 | 4.9 | −0.1 | 1.7 |
| 2 | 6.0 | 5.9 | 0.1 | −0.9 |
| 3 | 4.8 | 4.9 | −0.1 | 2.6 |
| 4 | 5.3 | 5.5 | −0.2 | 4.1 |
| 5 | 7.9 | 8.0 | −0.1 | 1.0 |
| 6 | 6.5 | 6.4 | 0.1 | −1.9 |
| 7 | 4.8 | 4.9 | −0.1 | 2.4 |
| 8 | 5.0 | 5.2 | −0.2 | 4.1 |
| 9 | 6.7 | 6.5 | 0.2 | −2.6 |
| 10 | 4.4 | 4.2 | 0.2 | −5.1 |
| 11 | 5.6 | 5.8 | −0.2 | 3.5 |
| 12 | 5.2 | 5.5 | −0.3 | 5.6 |
| 13 | 4.6 | 4.8 | −0.2 | 3.9 |
| 14 | 4.1 | 4.2 | −0.1 | 3.6 |
| 15 | 4.1 | 3.9 | 0.2 | −4.3 |
| 16 | 5.6 | 5.7 | −0.1 | 1.5 |
| 17 | 7.4 | 7.2 | 0.2 | −2.5 |
| 18 | 4.2 | 4.2 | 0.0 | −0.3 |
| 19 | 4.8 | 4.8 | 0.0 | 0.0 |
| 20 | 4.5 | 4.5 | 0.0 | 0.9 |
| 21 | 5.0 | 5.1 | −0.1 | 1.6 |
| 22 | 4.9 | 4.9 | 0.0 | 0.0 |
| 23 | 5.5 | 5.4 | 0.1 | −2.3 |
| 24 | 10.1 | 9.9 | 0.2 | −1.6 |
| 25 | 5.1 | 5.1 | 0.0 | −0.4 |
| 26 | 5.4 | 5.4 | 0.0 | 0.0 |
| 27 | 5.3 | 5.5 | −0.2 | 3.4 |
| 28 | 5.4 | 5.4 | 0.0 | 0.0 |
| 29 | 5.3 | 5.3 | 0.0 | 0.0 |
| 30 | 6.8 | 6.8 | 0.0 | −0.4 |
| 31 | 5.6 | 5.6 | 0.0 | 0.0 |
| 32 | 4.8 | 4.9 | −0.1 | 2.6 |
| 33 | 7.9 | 7.9 | 0.0 | 0.0 |
| 34 | 5.8 | 5.8 | 0.0 | 0.0 |
| 35 | 5.9 | 6.0 | −0.1 | 2.5 |
| 36 | 6.1 | 6.1 | 0.0 | 0.0 |
| 37 | 5.3 | 5.3 | 0.0 | 0.0 |
| 38 | 5.0 | 5.0 | 0.0 | 0.0 |
| 39 | 6.0 | 6.1 | −0.1 | 1.8 |
| 40 | 4.6 | 4.4 | 0.2 | −5.3 |

According to the NGSP certification procedures, 37 samples out of 40 should be located with +/−6% from the know standard assay. As shown in Table 5, the TRACE fulfils this criterion for NGSP certification (bias=within +/−6%).

Example 3. The HbA1c Precision Procedure

The Liquichek Diabetes control levels 1, 2 and 3 (BIO-RAD standard) were measured on TRACE for five days. Each control was measured four times per day. A total of 3×4×5=60 measurements were performed according to Examples 1 and 2.

The calibration was performed up against the Tina-quant HbA1c assay format and values were reported in NGSP units.

Table 6 displays the mean values and the intra and inter batch % CV display.

TABLE 6

| | Mean value in NGSP units | Within-run precision % (intra) | Between run precision % (inter) |
|---|---|---|---|
| Liquichek Diabetes control Level 1 (38481) | 5.68 (4.55-6.82) | 2.1 | 2.4 |
| Liquichek Diabetes control Level 2 (38482) | 9.58 (7.67-11.5) | 1.9 | 2.1 |
| Liquichek Diabetes control Level 3 (38483) | 13.6 (10.9-16.3) | 1.7 | 2.5 |

According to the NGSP programme, a recommendation of precision for the HbA1c assay should be below 3.5%. As shown in Table 6, the method according to the aspects of the disclosed embodiments fulfils this criterion for NGSP recommendations for the precision criteria.

Example 4. The HbA1c Final Signal Dependence of the Concentration of Fluorophore in the Sample Samples Six calibrator samples, all representing different levels of HbA1c concentration in human blood, were purchased from Lyphochek Haemoglobin A1c linearity set (BIO-RAD). The six samples from this BIO-RAD kit were dissolved according to the manufacturer's instructions.

The six linearity samples were measured on TRACE at three different concentrations of fluorophore added in step 1d of the method according to the aspects of the disclosed embodiments ($FLT_1$), and the final signal values are reported in Table 7.

TABLE 7

| Lyphochek Haemoglobin A1C linearity set (BIORAD) in IFCC values (mmol/mol) | Final HbA1c result ($FLT_1$) fluorescence signal = 3.200.000 = 3 ug fluorophore added in step 1d | Final HbA1c result ($FLT_1$) fluorescence signal = 3.900.000 = 4 ug fluorophore added in step 1d | Final HbA1c result ($FLT_1$) fluorescence signal = 4.600.000 = 5 ug fluorophore added in step 1d |
|---|---|---|---|
| Level 1 17, 1 | 57822 | 60163 | 69921 |
| Level 2 29, 5 | 89536 | 101658 | 106368 |
| Level 3 42, 3 | 131272 | 141051 | 146581 |
| Level 4 79, 1 | 292653 | 309582 | 303045 |
| Level 5 116 | 410252 | 423322 | 421829 |
| Level 6 161 | 538691 | 598343 | 591655 |

Table 7 displays the six linearity samples measured on TRACE at three different concentrations of fluorophore added in step 1d ($FLT_1$).

Figure 7:
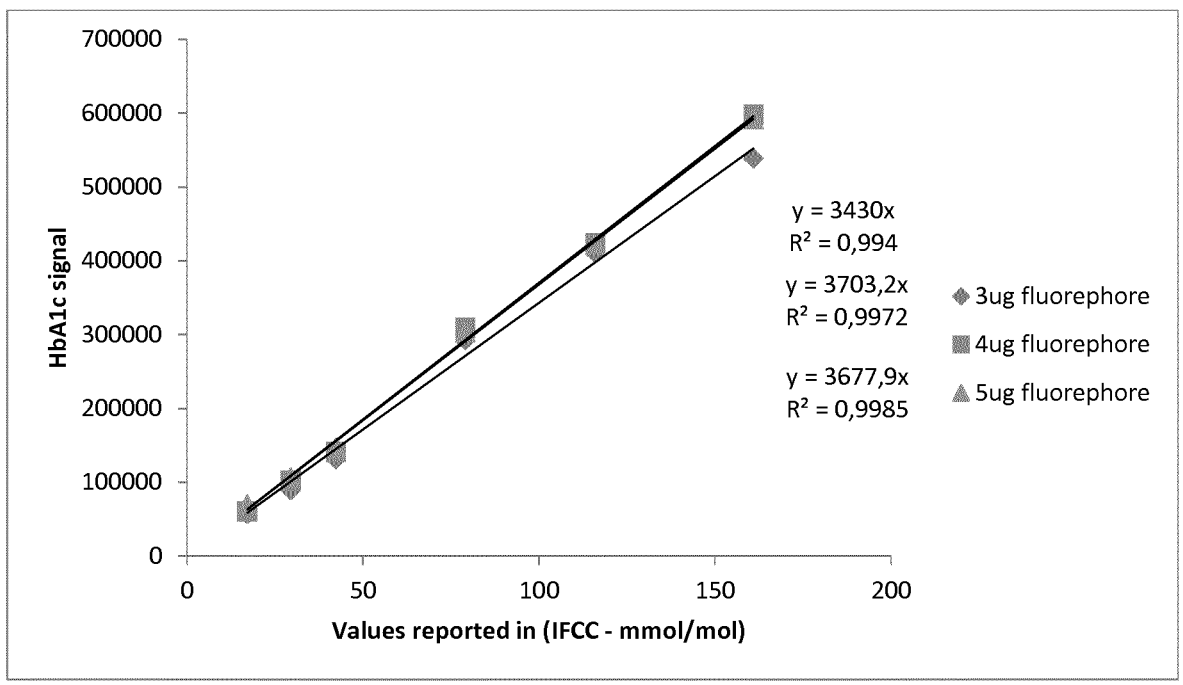
FIG. 7 graphically displays the contents of Table 7, where the TRACE HbA1c IFCC results from the six calibrators are displayed (x-axis) as a function of the final TRACE signal (y-axis) at three different concentration of the added fluorophore in step 1d.

It can be observed from Table 7 and FIG. 7 that the initial concentration of the added fluorophore influences the final HbA1c signal. Particularly, it is observed that a major difference exists between the six calibrators starting with the fluorophore concentration 3 ug compared to the six calibrators starting with the fluorophore concentration 4 ug.

The invention claimed is:

1. A method for determining a quantity of HbA1c relative to a total concentration of haemoglobin in a blood sample having a volume of less than 200 µl, the method comprising the steps of:
   a. providing a fluorophore comprising a ligand capable of binding HbA1c;
   b. providing a buffered liquid;
   c. measuring a first transmission ($TRT_0$) of the buffered liquid at time $T_0$ at a wavelength of approximately 570 nm and optionally measuring a first fluorescence ($FLT_0$) of the buffered liquid at a wavelength (X) at which the fluorophore emits fluorescent light when excited;
   d. adding the fluorophore to the buffered liquid, thereby creating a buffered reaction liquid, and optionally measuring a second fluorescence ($FLT_1$) of the buffered reaction liquid at time $T_1$ at the wavelength X;
   e. adding the blood sample to the buffered reaction liquid at time $T_2$, whereby a first detection liquid is formed comprising a fluorescence complex comprising the fluorophore and HbA1c, and measuring a third fluorescence ($FLT_{3,4}$) at the wavelength X of the first detection liquid at one or more time points within a time interval $T_3$-$T_4$, at which there is a change in fluorescence in the first detection liquid over time which is >0, reflecting that less than all HbA1c in the blood sample is part of said fluorescence complex in the first detection liquid;
   f. adding a haemoglobin-binding agent to the first detection liquid at time $T_5$, thereby creating a second detection liquid comprising a complex comprising the haemoglobin-binding agent and haemoglobin, and measuring a second transmission ($TRT_6$) of the second detection liquid at approximately 570 nm at time $T_6$;
   g. determining an absorbance of the blood sample by dividing the eond transmission ($TRT_6$) by the first transmission ($TRT_0$);
   h. determining the quantity of HbA1c relative to the total concentration of haemoglobin in the blood sample by dividing the third fluorescence ($FLT_{3,4}$) for the blood sample by the absorbance determined in step g) for the blood sample, and comparing obtained result from dividing the third fluorescence ($FLT_3$) for the blood sample by the absorbance determined in step g) with same data of an internal standard sample having known concentrations of HbA1c and haemoglobin.

2. The method according to claim 1, wherein an amount of fluorophore added to the liquid in step d) is determined by measuring the second fluorescence ($FLT_1$) of the liquid in step d), and the third fluorescence ($FLT_{3,4}$) is corrected for amount of fluorophore added.

3. The method according to claim 2, wherein the time interval $T_3$-$T_4$, is a time interval of 0-30 seconds after adding the sample to the buffered reaction liquid at time $T_2$.

4. The method according to claim 3, wherein the measurements of the third fluorescence ($FLT_{3,4}$), comprise measurements of at least two time points within the time interval $T_3$-$T_4$.

5. The method according to claim 3, wherein the time interval $T_3$-$T_4$, is a time interval of 0-20 seconds after adding the sample to the buffered reaction liquid at time $T_2$.

6. The method according to claim 2, wherein the measurements of the third fluorescence ($FLT_{3,4}$), comprise measurements of at least two time points within the time interval $T_3$-$T_4$.

7. The method according to claim 1, wherein the measurements of the third fluorescence ($FLT_{3,4}$), comprise measurements of at least two time points within the time interval $T_3$-$T_4$.

8. The method according to claim 7, wherein the measurements of the third fluorescence ($FLT_{3,4}$), comprise measurements of at least three time points within the time interval $T_3$-$T_4$.

9. The method according to claim 1, wherein the haemoglobin-binding agent is sodium lauryl sulphate (SDS).

10. The method according to claim 1, wherein the ligand is borate or boronic acid.

11. The method according to claim 1, wherein the fluorophore comprises eosin, and the fluorescence is measured at a wavelength X of approximately 570 nm.

12. The method according to claim 11, wherein the blood sample has a volume of less than 5 µl.

* * * * *